United States Patent
Atkinson et al.

(10) Patent No.: US 8,470,835 B2
(45) Date of Patent: Jun. 25, 2013

(54) PYRIMIDINECARBOXAMIDE DERIVATIVES AS INHIBITORS OF SYK KINASE

(75) Inventors: Francis Louis Atkinson, Harlow (GB); Vipulkumar Kantibhai Patel, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 13/144,136

(22) PCT Filed: Jan. 11, 2010

(86) PCT No.: PCT/EP2010/050228
§ 371 (c)(1), (2), (4) Date: Jul. 12, 2011

(87) PCT Pub. No.: WO2010/097248
PCT Pub. Date: Sep. 2, 2010

(65) Prior Publication Data
US 2011/0275655 A1 Nov. 10, 2011

Related U.S. Application Data

(60) Provisional application No. 61/144,210, filed on Jan. 13, 2009.

(51) Int. Cl.
*A01N 43/54* (2006.01)
*C07D 239/42* (2006.01)

(52) U.S. Cl.
USPC .......................................... 514/256; 544/315

(58) Field of Classification Search
USPC .......................................... 514/256; 544/315
See application file for complete search history.

(56) References Cited

FOREIGN PATENT DOCUMENTS

| EP | 1184376 A1 | 3/2002 |
|---|---|---|
| WO | 9931073 A1 | 6/1999 |
| WO | 2009136995 A2 | 11/2009 |

OTHER PUBLICATIONS

Pinedo et al. (2000).*
McMahon et al. (2000).*

* cited by examiner

*Primary Examiner* — Paul V. Ward
(74) *Attorney, Agent, or Firm* — Kathryn L. Coulter

(57) ABSTRACT

The present invention relates to the compound of formula (I):

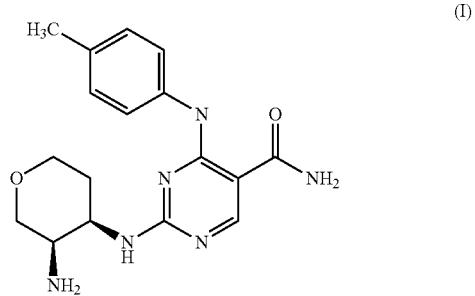

or a salt, preferably a pharmaceutically acceptable salt, thereof;

is an inhibitor of spleen tyrosine kinase (SYK) and therefore potentially of use in treating diseases resulting from inappropriate mast cell activation, for instance allergic and inflammatory diseases, as well of potential use in cancer therapy, specifically heme malignancies.

5 Claims, 1 Drawing Sheet

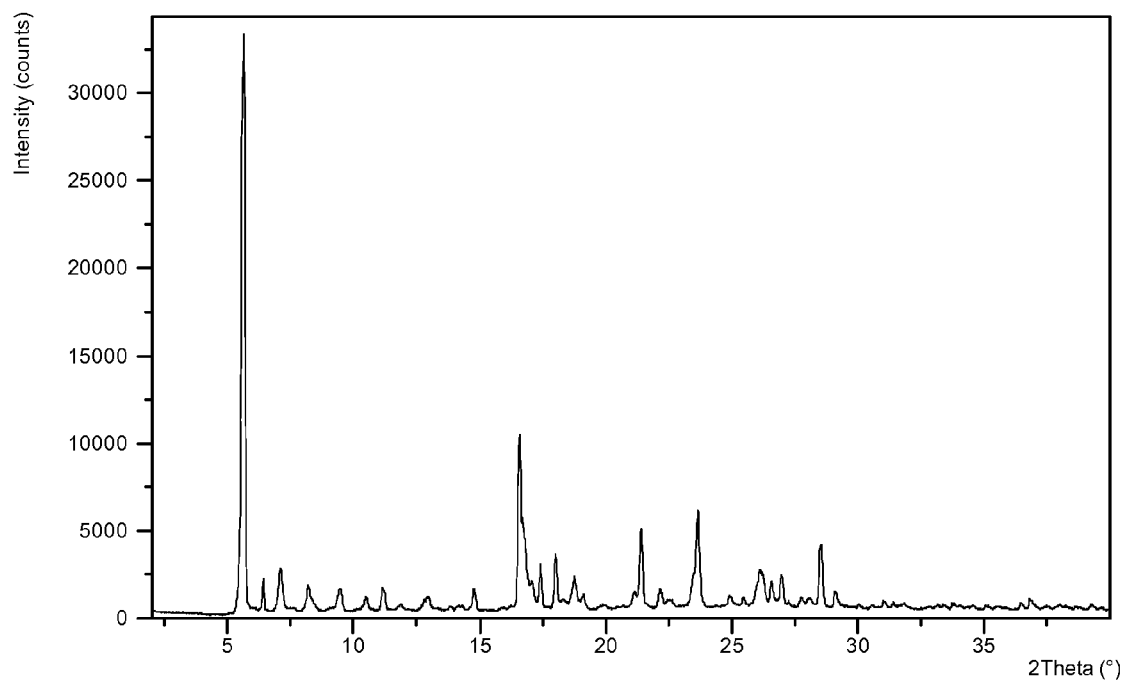
XPRD for the compound of Example 1.

PYRIMIDINECARBOXAMIDE DERIVATIVES AS INHIBITORS OF SYK KINASE

This application is filed pursuant to 35 U.S.C. §371 as a United States National Phase Application of International Patent Application No. PCT/EP2010/050228 filed Jan. 11, 2010, which claims priority from U.S. Provisional Application No. 61/144,210 filed Jan. 13, 2009.

The present invention relates to novel chemical compounds which have activity against the spleen tyrosine kinase (Syk kinase), processes for their preparation, pharmaceutically acceptable formulations containing them and their use in therapy.

Syk kinase is a non-receptor tyrosine kinase that is involved in coupling activated immunoreceptors to signal downstream events that mediate diverse cellular responses, including proliferation, differentiation, and phagocytosis. Syk kinase is widely expressed in hematopoietic cells. Syk kinase inhibitors have potential anti-inflammatory and immunomodulating activities. They inhibit Syk kinase-mediated IgG Fc epsilon and gamma receptor and BCR receptor signaling, resulting in inhibition of the activation of mast cells, macrophages, and B-cells and related inflammatory responses and tissue damage. Accordingly, Syk kinase inhibitors have attracted interest in a number of therapeutic areas, including the treatment of rheumatoid arthritis, B-cell lymphoma and asthma/rhinitis.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al 2004, New Eng. J. Med. 350: 2572-2581), have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease Studies using cells from mice deficient in the Syk kinase have demonstrated a non-redundant role of this kinase in B cell function. The deficiency in Syk kinase is characterised by a block in B cell development (M. Turner et al 1995 Nature 379: 298-302 and Cheng et al 1995, Nature 378: 303-306). These studies, along with studies on mature B cells deficient in Syk kinase (Kurasaki et al 2000, Immunol. Rev. 176:19-29), demonstrate that Syk kinase is required for the differentiation and activation of B cells. Hence, inhibition of Syk kinase in RA patients is likely to block B cell function and hence to reduce Rheumatoid Factor production. In addition to the role of Syk kinase in B cell function, of relevance to the treatment of RA, is the requirement for Syk kinase activity in Fc receptor (FcR) signalling. FcR activation by immune complexes in RA has been suggested to contribute to the release of multiple pro-inflammatory mediators.

The contribution of Syk kinase dependent processes to the pathology of RA has been reviewed by Wong et al (2004, ibid).

The results of a 12 week clinical trial for the syk kinase inhibitor R788 (fostamatinib disodium, Rigel) have been published: Treatment of rheumatoid arthritis with a syk kinase inhibitor: A twelve-week, randomized, placebo-controlled trial, Arthritis & Rheumatis, 58(11), 2008, 3309-3318.

Syk inhibitors may also be useful in cancer therapy, specifically heme malignancies, particularly Non-Hodgkin's Lymphomas including follicular (FL), mantle cell, Burkitt and diffuse large B cell (DLBCL) lymphomas.

Studies have shown that Syk is dysregulated by overexpression and/or constitutively activation in a variety of primary B-lymphoma tumors and also in B-lymphoma cell lines. Syk, through the PI3K/AKT pathway, the PLD pathway and AKT independent signalling, activates mTOR (mammalian target of rapamycin) which in turn increases B-cell survival and proliferation. Inhibition of Syk, in vitro, results in decreased mTOR activation and a reduction of clonicity in FL cells. Inhibition of Syk kinase with curcumin in a murine model of B lymphoma (BKS-2) gave a significant reduction of tumour burden as measured by the total splenocyte number. (Leseux L. et al. Blood 15 Dec. 2006, Vol 108, No 13 pp 4156-4162 and Gururajan M. et al. Journal of Immunology, 2007, 178 pp 111-121).

Results of a Phase 2 clinical trial of R788 (fostamatinib disodium) in patients with relapsed or refractory B-Cell non-Hodgkin's lymphoma (NHL) show that the compound is well-tolerated by these patients, as well as a therapeutic benefit in patients suffering from diffuse large B-Cell lymphoma (DLBCL) and chronic lymphocytic leukemia/small lymphocytic lymphoma (CLL/SLL). Despite the fact that the patients enrolled in this trial had advanced disease and had failed treatment with marketed therapies, a significant number of them were particularly responsive to Syk inhibition with R788 (www.Riqel.com)

Syk inhibitors may also be useful in the treatment of asthma and rhinitis as they are important in transducing the downstream cellular signals associated with cross-linking FcεR1 and or FcγR1 receptors, and is positioned early in the signalling cascade. In mast cells, for example, the early sequence of FcεR1 signalling following allergen cross-linking of receptor-IgE complexes involves first Lyn (a Src family tyrosine kinase) and then Syk kinase.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE (FcεRI) and IgG (FcγRI) become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesised lipid mediators including prostaglandins and leukotrienes.

The Syk kinase inhibitor R112 (Rigel), dosed intranasally in a phase I/II study for the treatment of allergic rhinitis, was shown to give a statistically significant decrease in $PGD_2$, a key immune mediator that is highly correlated with improvements in allergic rhinorrhea, as well as being safe across a range of indicators, thus providing the first evidence for the clinical safety and efficacy of a topical Syk kinase inhibitor (see Meltzer, Eli O.; Berkowitz, Robert B.; Grossbard, Elliott B. An intranasal Syk kinase inhibitor (R112) improves the symptoms of seasonal allergic rhinitis in a park environment. Journal of Allergy and Clinical Immunology (2005), 115(4), 791-796). In a further phase II clinical trial, for allergic rhinitis, R112 was however shown as having a lack of efficacy versus placebo (Clinical Trials.gov Identifier NCT0015089).

EP1184376B1/WO200007513 and EP1054004/WO9903101073 (Yamanouchi Pharmaceutical Co Ltd) describe novel heterocyclic carboxamide derivatives that have Syk inhibitory activity. These are further described in "Synthetic studies on novel Syk Inhibitors. Part 1: Synthesis and structure-activity relationships of 5-pyrimidine-5-carboxamidr derivatives (H. Hisamichi et al, Bioorg Med Chem 13 (2005) 4936-4951). In particular, it would appear from this paper that the preferred compound is the compound of formula (A):

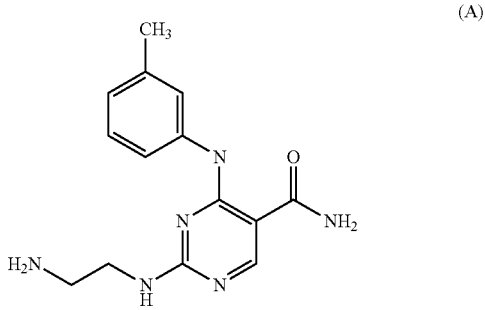 [SMILES: Cc1cccc(Nc2nc(NCCN)ncc2C(N)=O)c1]

The scope of WO9903101073 describes a wider range of analogues, including a set in which the ethylene diamine moiety is replaced by cis-1,2-diaminocyclohexyl.

WO 04/035604 discloses the structural co-ordinates of the human Syk protein.

There remains however the need to identify further compounds which are inhibitors of Syk kinase.

Thus, in a first aspect invention, the present invention provides a compound of formula (I):

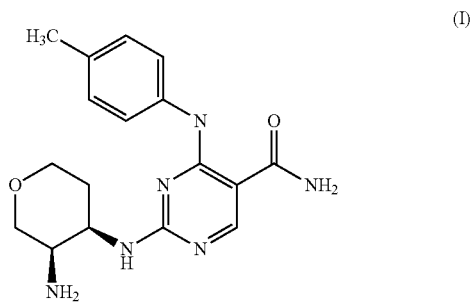 [SMILES: Cc1ccc(Nc2nc(N[C@@H]3CCOC[C@@H]3N)ncc2C(N)=O)cc1]

or a salt, preferably a pharmaceutically acceptable salt, thereof.

The compound of formula (I) has the chemical name:
2-{[(3R,4R)-3-aminotetrahydro-2H-pyran-4-yl]amino}-4-[(4-methylphenyl)amino]-5-pyrimidinecarboxamide.

Compounds of the present invention are useful as inhibitors of Syk. Compounds of the present invention also exhibit selectivity for the Syk kinase against other key kinases, for instance at least 10× (based on either pKi or $piC_{50}$ values for the enzymes), in particular the kinases VEGFR2 and Aurora B. Compounds of the present invention also exhibit low activity in the hERG assay, a key measure of potential cardiac toxicity.

Compounds of the present invention are thus potentially of use in treating some cancer therapies, in particular heme malignancies, as well as inflammatory conditions which involve B cells and/or activated macrophages, and also diseases resulting from inappropriate mast cell activation, for instance allergic and inflammatory diseases.

BRIEF DESCRIPTION OF THE DRAWINGS

FIG. 1 illustrates the XPRD data for the compound of Example 1 as described in Example 1.

When used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio. The skilled artisan will appreciate that pharmaceutically acceptable salts of the compound of the present invention may be prepared.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively. Indeed, in certain embodiments of the invention, pharmaceutically acceptable salts may be preferred over the respective free base or free acid because such salts impart greater stability or solubility to the molecule thereby facilitating formulation into a dosage form.

The compound of formula (I) is basic and accordingly generally capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

A compound of the present invention may exist in solid or liquid form. In the solid state, the compound of the present invention may exist in crystalline or non-crystalline (amorphous) form, or as a mixture thereof. For a compound of the present invention that is in crystalline form, the skilled artisan will appreciate that pharmaceutically acceptable solvates may be formed wherein solvent molecules are incorporated into the crystalline lattice during crystallization. Solvates may involve non-aqueous solvents such as, but not limited to, ethanol, isopropanol, n-butanol, i-butanol, acetone, tetrahydrofuran, dioxane, DMSO, acetic acid, ethanolamine, and ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that a compound of the present invention that exists in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compound of formula (I), thereof, may be prepared by the general synthetic scheme described hereinafter.

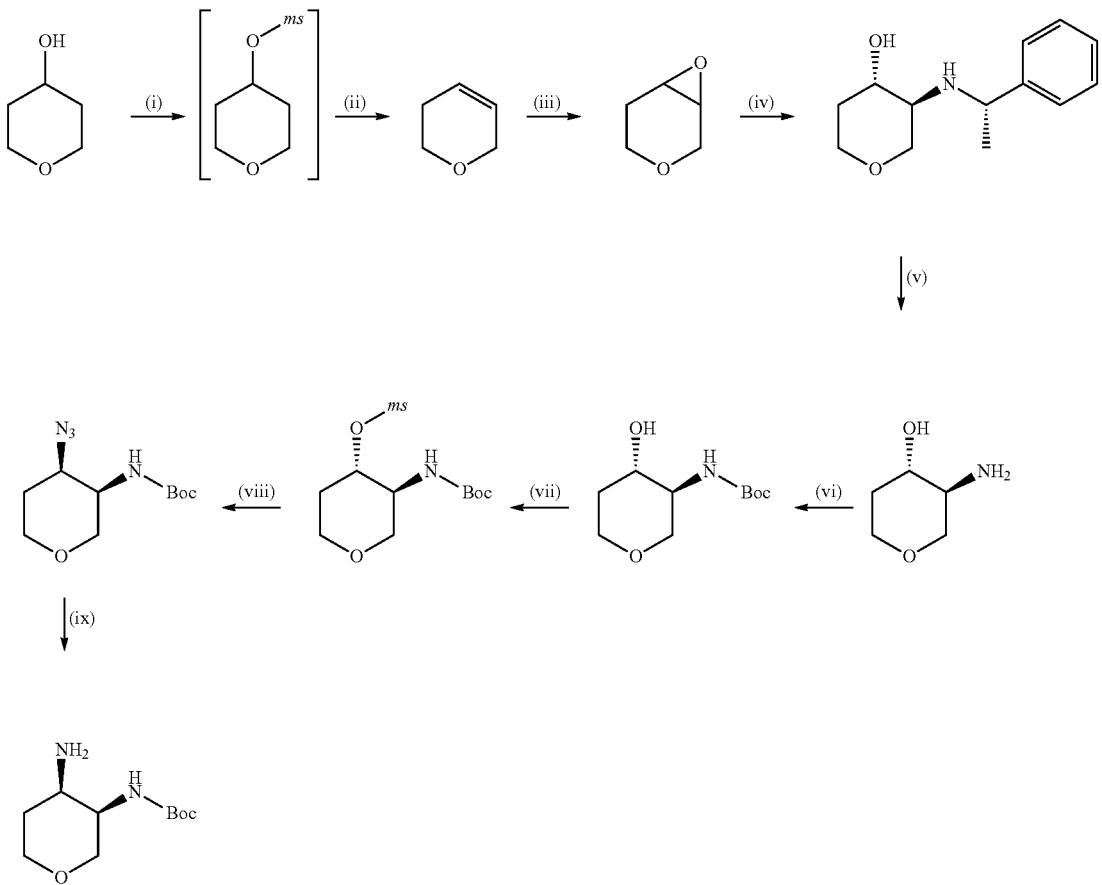

(i) Mesyl chloride, Et₃N, DCM;
(ii) DBU;
(iii) mCPBA, CHCl₃;
(iv) [(1S)-1-phenylethyl]amine, 2-PrOH/70° C. or 2-BUOH/90° C.;
(v) Pd(OH)₂/C, H₂, EtOH;
(vi) (Boc)₂O, Et₃N, MeOH;
(vii) Mesyl chloride, Et₃N, DCM;
(viii) NaN₃, NaOAc, DMF;
(ix) PrO₂, H₂, EtOH.

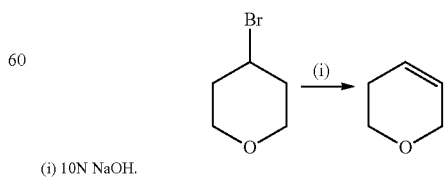

(i) 10N NaOH.

Scheme 3

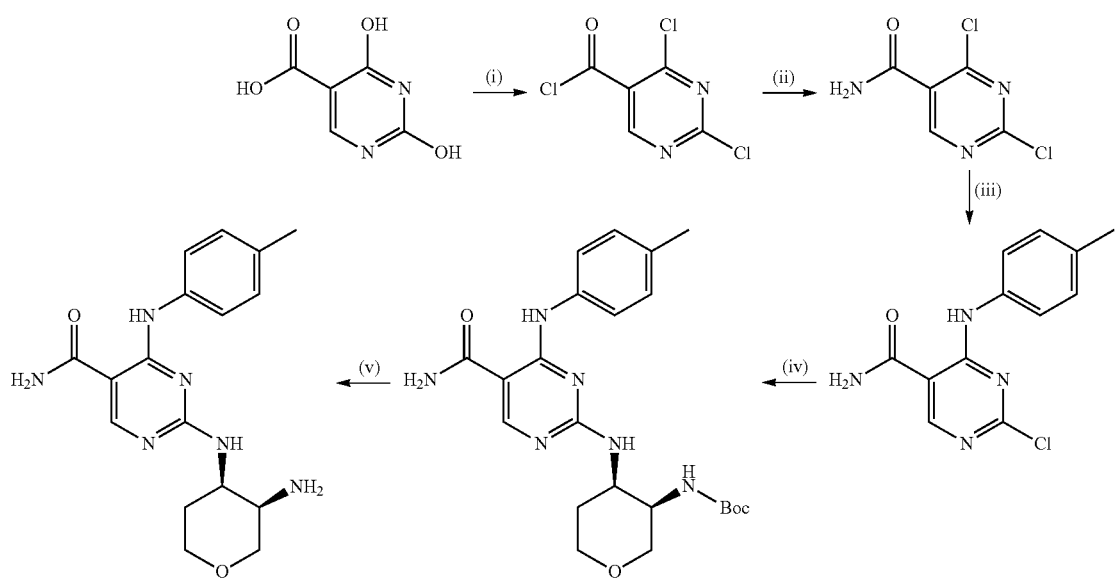

(i) PCl₅;
(ii) NH₃, 1,4-dioxane;
(iii) P-toluidine, Et₃N, DMF;
(iv) 1,1-dimethylethyl [(3R,4R)-4-aminotetrahydro-2H-pyran-3-yl]carbamate, Et₃N, DMF;
(v) HCl / isopropanol.

Accordingly, in a further aspect, the present invention provides a process for preparing a compound of formula (I) which process comprises treating a compound of formula (II):

(II)

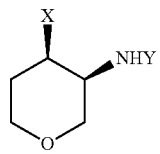

with a compound of formula (III):

(III)

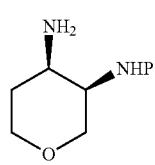

where P is a protecting group eg t-butoxycarbonyl (Boc), and thereafter, removing the protecting group.

The following intermediate compounds of formula (IV):

(IV)

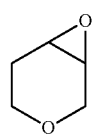

wherein X is N₃ or NH₂ and Y is a protecting group, for instance t-butoxycarbonyl (Boc), and which has the (3R,4R) stereochemistry;
are novel and of use in the preparation of compounds of formula (I) and therefore provide a further aspect of the invention.

An important aspect in the preparation of a compound of formula (III) and (IV) is the introduction of the appropriate stereochemistry at C-3 and C-4. It is found that this can be advantageously effected by the regiospecific opening of the epoxide of formula (V):

(V)

at C-3, by reaction with a chiral amine precursor, such as [(1S)-1-phenylethyl]amine, in a C₂₋₄ alcohol, preferably a secondary alcohol, such as 2-propanol or 2-butanol, at an elevated temperature, preferably under reflux conditions. The reaction may also be carried out in the presence of trimethylaluminium, in a solvent such as dichloromethane, followed by work-up with sodium fluoride, to decompose the aluminate. The initial reaction product is potentially a mixture of two C-3 diastereoisomers and two C-4 diastereoisomers, the C-3:C-4 ratio depending on the regiospecificity of the epoxide ring opening. The C-3 regioisomer mixture may then be separated out and the chiral moiety removed, to give the desired 3-amino, 4-hydroxy tetrahydropyran intermediate of formula (VI):

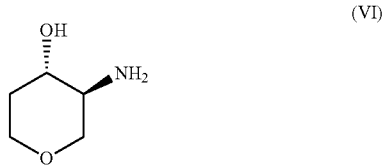

(VI)

in high enantiomeric purity.

Accordingly, in a further aspect, the present invention provides for the preparation of a compound of formula (IV) or (IV), which processes comprises the step of reacting the compound of formula (V) with with a chiral amine precursor, such as [(1S)-1-phenylethyl]amine, in a $C_{2-4}$ alcohol, preferably a secondary alcohol, such as 2-propanol or 2-butanol, at an elevated temperature, preferably under reflux conditions.

It will be appreciated that in some instances it may be useful to employ a protecting group. Examples of protecting groups and the means for their removal can be found in T. W. Greene 'Protective Groups in Organic Synthesis' (J. Wiley and Sons, 1991). Suitable amine protecting groups include, but are not restricted to, sulphonyl (such as tosyl), acyl (such as benzyloxycarbonyl or t-butoxycarbonyl) and arylalkyl (such as benzyl), which may be removed by hydrolysis or hydrogenolysis as appropriate. Other suitable amine protecting groups include trifluoroacetyl (—C(O)CF$_3$), which may be removed by base catalysed hydrolysis, or a solid phase resin bound benzyl group, such as a Merrifield resin bound 2,6-dimethoxybenzyl group (Ellman linker) which may be removed by acid catalysed hydrolysis (using, for example, trifluoroacetic acid).

Compounds of the present invention are useful as inhibitors of Syk and thus potentially of use in treating some cancer therapies, in particular heme malignancies, as well as inflammatory conditions which involve B cells, and also diseases resulting from inappropriate mast cell activation, for instance allergic and inflammatory diseases.

Thus, in a further aspect, the present invention provides for a compound of formula (I), or a pharmaceutically acceptable salt thereof, for use in therapy.

In a further aspect, the present invention provides a method comprising administering to a patient in need thereof an effective amount of a compound of formula (I), or a pharmaceutically acceptable salt thereof, to inhibit a Syk kinase.

Syk inhibitors may be useful in cancer therapy, specifically heme malignancies, particularly Non-Hodgkin's Lymphomas including follicular (FL), mantle cell, small lymphocytic lymphoma/chronic lymphocytic lymphoma (SLL/CLL), Burkitt and diffuse large B cell (DLBCL) lymphomas.

Accordingly, in a further aspect, the present invention provides for a method of treating cancer, specifically heme malignancies, particularly Non-Hodgkin's Lymphomas including follicular (FL), mantle cell, Burkitt and diffuse large B cell (DLBCL) lymphomas, which method comprises administering to a patient in need thereof an effective amount of a compound of formula (I), or a pharmaceutically acceptable salt thereof.

Compounds of the present invention may also be used in cancer chemotherapy in combination with other classes of cancer chemotherapy agents which are known in the art. Representative classes of agents for use in such combinations for Non-Hodgkin's Lymphomas include ritaximab, BEXXAR (tositumomab and Iodine I 131 tositumomab), pixantrone and chemotherapy. Combination of compounds of the present invention may also be used in combination with the CHOP drug regime (Cyclophosphamide, Adriamycin, Vincristine, Prednisone) or CHOP plus ritaximab (CHOP+R).

Compounds of the present invention are potentially of use in treating auto immune conditions which involve B cells and/or macrophage activation, for instance systemic lupus erythematosus, Sjorgens Syndrome, Wegners granulomatosis, Bullous Pemphigoid, Idiopathic Thrombocytopenic Purpura (ITP), Giant Cell Arteriosis, Chronic Idiopathic Urticaria with and without auto-antibody status (Chronic Autoimmune Urticaria) (New concepts in chronic urticaria Current Opinions in Immunology 2008 20:709-716), Glomerulonephritis, Chronic Transplant Rejection, and rheumatoid arthritis.

In a further aspect, the present invention provides a method of treating an inflammatory disease which involves B cells which method comprises administering to a patient in need thereof an effective amount of a compound of formula (I), or a pharmaceutically acceptable salt thereof.

Compounds of the present invention are potentially of use in treating diseases resulting from inappropriate mast cell activation, for instance allergic and inflammatory diseases.

In a further aspect, the present invention provides for a method of treating inappropriate mast cell activation which method comprises administering to a patient in need thereof an effective amount of a compound of formula I, or a pharmaceutically acceptable salt thereof.

In a further aspect, the present invention provides a method of treating an inflammatory disease which method comprises administering to a patient in need thereof an effective amount of a compound of formula (I), or a pharmaceutically acceptable salt thereof.

In a further aspect, the present invention provides a method of treating an allergic disorder which comprises administering to a patient in need thereof an effective amount of a compound of formula (I), or a pharmaceutically acceptable salt thereof.

Diseases and pathological conditions thought to be mediated by Syk kinase include inflammatory and allergic disorders involving mast cell activation, such as chronic obstructive pulmonary disease (COPD), adult respiratory distress syndrome (ARDS), asthma, ulcerative colitis, Crohn's Disease, bronchitis, conjunctivitis, psoriasis, sclerodoma, urticaria, dermatitis, and allergic rhinitis.

Compounds of the present invention may also be used in combination with other classes of therapeutic agents which are known in the art. Representative classes of agents for use in such combinations include, for treating asthma, anti-inflammatory steroids (in particular corticosteroids), PDE4 inhibitors, IKK2 inhibitors, A2a agonists, $\beta_2$-adrenoreceptor agonists (including both short acting and long acting $\beta_2$-adrenoreceptor agonists), alpha 4 integrin inhibitors, and anti-muscarinics, and, for treating allergies, the foregoing agents, as well as histamine receptor antagonists, including H1 and H1/H3 antagonists. Representative agents for use in combination therapy for treating severe asthma include topically acting p38 inhibitors, and IKK2 inhibitors.

Anti-inflammatory corticosteroids are well known in the art. Representative examples include fluticasone propionate (e.g. see U.S. Pat. No. 4,335,121), beclomethasone 17-propionate ester, beclomethasone 17,21-dipropionate ester, dexamethasone or an ester thereof, mometasone or an ester thereof (e.g. mometasone furoate), ciclesonide, budesonide, and flunisolide. Further examples of anti-inflammatory corticosteroids are described in WO 02/12266 A1 (Glaxo Group Ltd), in particular, the compounds of Example 1 (6α,9α-difluoro-17α-[(2-furanylcarbonyl)oxy]-11β-hydroxy-16α-methyl-3-oxo-androsta-1,4-diene-17β-carbothioic acid S-fluoromethyl ester) and Example 41 (6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester), or a pharmaceutically acceptable salt thereof.

Examples of $\beta_2$-adrenoreceptor agonists include salmeterol (e.g. as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 24 hour period such as salmeterol or formoterol.

Examples of anti-histamines include methapyrilene, or loratadine, cetirizine, desloratadine or fexofenadine.

Examples of anticholinergic compounds include muscarinic (M) receptor antagonists, in particular $M_1$, $M_2$, $M_1/M_2$, or $M_3$ receptor antagonists, in particular a (selective) $M_3$ receptor antagonist. Examples of anticholinergic compounds are described in WO 03/011274 A2 and WO 02/069945 A2/US 2002/0193393 A1 and US 2002/052312 A1. Examples of muscarinic M3 antagonists include ipratropium bromide, oxitropium bromide or tiotropium bromide.

Representative PDE4 or mixed PDE3/4 inhibitors that may be used in combination with compounds of the invention include AWD-12-281 (Elbion), PD-168787 (Pfizer), roflumilast, and cilomilast (GlaxoSmithKline). Further examples of PDE4 inhibitors are described in WO 2004/103998, WO2005/030212, WO2005/030725, WO2005/058892, WO2005/090348, WO2005/090352, WO2005/090353, WO2005/090354, WO2006/053784, WO2006/097340, WO2006/133942, WO2007/036733, WO2007/036734 and WO2007/045861 (Glaxo Group Ltd).

The present invention also provides for so-called "triple combination" therapy, comprising a compound of formula (I) or a pharmaceutically acceptable salt thereof together with $\beta_2$-adrenoreceptor agonist and an anti-inflammatory corticosteroid. Preferably this combination is for treatment and/or prophylaxis of asthma, COPD or allergic rhinitis. The $\beta_2$-adrenoreceptor agonist and/or the anti-inflammatory corticosteroid can be as described above and/or as described in WO 03/030939 A1. A representative example of such a "triple" combination comprises a compound of formula (I) or a pharmaceutically acceptable salt thereof, salmeterol or a pharmaceutically acceptable salt thereof (e.g. salmeterol xinafoate) and fluticasone propionate.

The compound of the present invention will normally, but not necessarily, be formulated into pharmaceutical compositions prior to administration to a patient. Accordingly, in another aspect the invention is directed to pharmaceutical compositions comprising a compound of the invention and one or more pharmaceutically acceptable excipient.

The pharmaceutical compositions of the invention may be prepared and packaged in bulk form wherein a safe and effective amount of a compound of the invention can be extracted and then given to the patient, such as with powders or syrups. Alternatively, the pharmaceutical compositions of the invention may be prepared and packaged in unit dosage form wherein each physically discrete unit contains a safe and effective amount of a compound of the invention. The pharmaceutical compositions of the invention may also be prepared and packaged in a sub-unit dosage form wherein two or more sub-unit dosage forms provide the unit dosage form. When prepared in unit dosage form, the pharmaceutical compositions of the invention typically contain from about 0.1 to 99.9 wt. %, of the compound of the invention, depending on the nature of the formulation.

In addition, the pharmaceutical compositions of the invention may optionally further comprise one or more additional pharmaceutically active compounds.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions are avoided. In addition, each excipient must of course be of sufficiently high purity to render it pharmaceutically acceptable.

Compositions of the present invention comprising a compound of the invention and the pharmaceutically acceptable excipient or excipients will typically be provided as a dosage form adapted for administration to the patient by the desired route of administration. For example, dosage forms include those adapted for (1) inhalation, such as aerosols and solutions; (2) intranasal administration, such as solutions or sprays; (3) oral administration, such as tablets, capsules, caplets, pills, troches, powders, syrups, elixers, suspensions, solutions, emulsions, sachets, and cachets; and (4) parenteral administration, such as sterile solutions, suspensions, and powders for reconstitution.

It will be appreciated that dosage forms adapted for inhalation or oral administration are commonly used for treating COPD; dosage forms adapted for intranasal administration are commonly used for treating allergic rhinitis; and dosage forms adapted for oral administration are commonly used for treating rheumatoid arthritis and heme malignancies.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: Diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), Remington: The Science and Practice of Pharmacy, (Lippincott Williams & Wilkins), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

Oral solid dosage forms such as tablets will typically comprise one or more pharmaceutically acceptable excipients, which may for example help impart satisfactory processing and compression characteristics, or provide additional desirable physical characteristics to the tablet. Such pharmaceutically acceptable excipients may be selected from diluents, binders, glidants, lubricants, disintegrants, colorants, flavorants, sweetening agents, polymers, waxes or other solubility-modulating materials.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided]. The pH of such IV fluids may vary, and will typically be from 3.5 to 8 as known in the art.

Dosage forms for nasal or inhaled administration may conveniently be formulated as aerosols, solutions, drops, gels or dry powders.

Dosage forms for topical administration to the nasal cavity (nasal administration) include pressurised aerosol formulations and aqueous formulations administered to the nose by pressurised pump. Formulations which are non-pressurised and adapted for nasal administration are of particular interest. Suitable formulations contain water as the diluent or carrier for this purpose. Aqueous formulations for administration to the nose may be provided with conventional excipients such as buffering agents, tonicity modifying agents and the like. Aqueous formulations may also be administered to the nose by nebulisation.

In a further embodiment, dosage forms for nasal administration are provided in a metered dose device. The dosage form may be provided as a fluid formulation for delivery from a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. In one embodiment, the fluid dispenser is of the general type described and illustrated in WO-A-2005/044354. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

For compositions suitable and/or adapted for inhaled administration, it is preferred that the compound or salt of formula (I) is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction).

Aerosol compositions, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of formula (I) or salt or solvate thereof (preferably in particle-size-reduced form, e.g. in micronised form), and optionally a performance modifier such as L-leucine or another amino acid, cellobiose octaacetate and/or metals salts of stearic acid such as magnesium or calcium stearate. Preferably, the dry powder inhalable composition comprises a dry powder blend of lactose and the compound of formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. Most importantly, it is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 JD Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS™ device, marketed by GlaxoSmithKline. The DISKUS™ inhalation device is for example described in GB 2242134 A, and in such a device at least one container for the pharmaceutical composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the pharmaceutical composition in powder form from the opened container.

A composition of the present invention, for intranasal administration, may also be adapted for dosing by insufflation, as a dry powder formulation.

It will be appreciated that when the compound of the present invention is administered in combination with other therapeutic agents normally administered by the inhaled, intravenous, oral or intranasal route, that the resultant pharmaceutical composition may be administered by the same routes.

The compound of the present invention may conveniently be administered in amounts of, for example, 1 µg to 2 g. The precise dose will of course depend on the age and condition of the patient and the particular route of administration chosen.

Biological Test Methods

Compounds of the invention may be tested for in vitro activity in accordance with the following assays:
Basic Enzyme Activity
1. Syk Enzyme Assay—Time-resolved Fluorescence Resonance Energy Transfer Kinase Assay Recombinant human Syk was expressed as a His-tagged protein*. The activity of Syk was assessed using a time-resolved fluorescence resonance energy transfer (TR-FRET) assay.
Preparation of Recombinant Human Full Length Spleen Tyrosine Kinase (Syk)
Syk Syk was pre-activated at room temperature for 30 mins in the presence of 16.6 mM $MgCl_2$, 8.3 mM ATP and then diluted to 4 nM in 40 mM Hepes pH 7.4, 0.01% BSA. 3 µl of substrate reagent containing biotinylated peptide, Biotin-AAAEEIYGEI (0.5 µM final), ATP (30 µM final) and $MgCl_2$ (10 mM final) in 40 mM HEPES pH 7.4, 0.01% BSA, were added to wells containing 0.1 µl of various concentrations of compound or DMSO vehicle (1.7% final) in Greiner low volume 384 well black plate. The reaction was initiated by the addition of 3 µl of diluted Syk (2 nM final). The reaction was incubated for 60 min at room temperature, then terminated by the addition of 3 µl of read reagent containing 60 mM EDTA, 150 mM NaCl, 50 nM Streptavidin APC (Prozyme, San Leandro, Calif., USA), 0.5 nM antiphosphotyrosine antibody labelled with W-1024 europium chelate (Wallac OY, Turku, Finland) in 40 mM HEPES pH 7.4, 0.03% BSA. The reaction was further incubated for 45 min at room temperature. The degree of phosphorylation of Biotin-AAAEEIYGEI was measured using a BMG Rubystar plate reader (BMG LabTechnologies Ltd, Aylesbury, UK) as a ratio of specific 665 nm energy transfer signal to reference europium 620 nm signal.

The compound of formula (I) has an $IC_{50}$ value in this assay of 40 nM.

Full length human Syk was expressed with a 6His tag on the N-terminal using the baculovirus system (Invitrogen, Paisley, Scotland). The cells were disrupted by dounce homogenisation, the debris removed by centrifugation and the lysate contacted with NiNTA Superflow (Qiagen, Crawley, UK). The NiNTA was packed into a column and eluted using 10 column volumes each of buffer (20 mM Tris pH8.0, 300 mM NaCl, 10 mM βMcEtOH, 10% glycerol), buffer+1M NaCl, buffer+20 mM Imidazole and buffer+300 mM imidazole. The 300 mM Imidazole fractions were pooled buffer exchanged using G25M (Amersham Biosciences, Buckinghamshire, UK) into 20 mM MES pH 6.0, 20 mM NaCl, 10 mM βMcEtOH, 10% glycerol. The buffer exchanged 6His-Syk was loaded onto a Source 15S column (Amersham Biosciences, Buckinghamshire, UK) and the column eluted using a NaCl gradient 0-500 mM over 50 column volumes. The 6His-Syk containing fractions were pooled and concentrated by ultra-filtration. The identity of 6His-Syk was confirmed by peptide mass finger printing and intact LC-MS.
Kinase Selectivity
2. Aurora B Enzyme Assay—Fluorescence Polarisation Kinase Assay Recombinant human Aurora B (2-344) was expressed as a Flag-6His-Thr-tagged protein*. The activity of Aurora B was assessed using a Fluorescence Polarisation IMAP assay (Molecular Devices, Sunnyvale, US).
*Preparation of Recombinant Human Full Length Aurora B Aurora B (2 µM) was preactivated by equivalent concentration of GST-INCENP[§] in 30 mM Tris-HCl pH 8.0, 0.4 mM ATP, 2 mM $MgCl_2$, 0.1 mM EGTA, 0.1% BME (beta mercaptoethanol), 0.1 mM sodium vanadate, 10 mM DTT for 3 hours at 30° C. This solution was then dialysed for 5 hours against 50 mM Tris-HCl, pH 7.5, 270 mM sucrose, 150 mM NaCl, 0.1 mM EDTA, 0.1% BME, 1 mM benzamidine and 0.2 mM PMSF at 4° C. Aurora B/INCENP complex was aliquoted and frozen at −80° C.

[§]Human INCENP (826-919) clone DU930 was received from University of Dundee, it is a GST N-terminal tagged protein.

A final concentration of 2 nM of Aurora B/INCENP complex was added to the assay buffer (25 mM HEPES, 25 mM NaCl 0.0025% Tween-20, pH 7.2 0.015% BSA, 1 µM DTT). 3 µl of this solution was added to wells containing 0.1 µl of various concentrations of compound or DMSO vehicle in Greiner low volume 384 well black plate at room temperature for 30 mins. The reaction was initiated by the presence of 3 µl of substrate reagent containing 100 nM 5FAM-PKA-tide (GRTGRRNSI-NH$_2$), 2 µM ATP and 2 mM MgCl$_2$ in assay buffer (25 mM HEPES, 25mM NaCl 0.0025% Tween-20, pH 7.2 0.015% BSA, 1 µM DTT) with a final DMSO level of 1.7%. The reaction was incubated for a further 120 mins at room temperature, and then terminated by the addition of 6 µl of a 1:500 dilution Progressive Binding Reagent solution (Part: R7287) in the manufacturers buffer A (Part: R7285) and manufacturers buffer B (Part R7286) and left to incubate for 120 mins at room temperature. The degree of phosphorylation of the 5FAM-PKA-tide (GRTGRRNSI-NH$_2$) was measured using an Acquest plate reader (Molecular Devices, Sunnyvale, US) with excitation 485 nM, emission at 530 nM and using a 505 nmM dichroic lens. Data was captured in parallel and perpendicular directions and converted to mp by the instrument.

The compound of formula (I) has an activity in this assay of 20 µM.

Full length human Aurora B was expressed with a 6His tag on the N-terminal region using the baculovirus system (Invitrogen, Paisley, Scotland). The sf9 cells were lysed by sonication, the debris removed by centrifugation and the lysate contacted with NiNTA Superflow (Qiagen, Crawley, UK). The NiNTA was packed into a column and eluted using 1-300 mM imidazole gradient. The 300 mM Imidazole fractions were pooled and dialysed against 50 mM Tris-HCl, pH 8.0, 250 mM NaCl and 2 mM DTT to remove imidazole. Approximately 60% pure protein was recovered after dialysis. The identity of Aurora B was confirmed by N-terminal sequence analysis and LC-MS.

3. VEGFR2 (KDR) Enzyme Assay—Time-resolved Fluorescence Resonance Energy Transfer Kinase Assay Recombinant human VEGFR2 (KDR) intracellular domain (including the entire kinase domain) was expressed as a GST-6His-tagged protein*. The activity of VEGFR2 was assessed using a time-resolved fluorescence resonance energy transfer (TR-FRET) assay. Test compounds at the desired concentrations in 100% DMSO or 100% DMSO vehicle were added in 0.1 µL to a Greiner low-volume, 384-well, black plate (#784076). The plate was centrifuged minimally at 1000 RPM for 1 min. to force all of the liquid to the bottom of the wells prior to addition of any assay reagents.

*Purification of Recombinant GST-6His-VEGFR2

VEGFR2 (100 nM typically) was activated at room temperature for 20 min. in the presence of 100 mM HEPES, pH 7.5, 10 mM MgCl$_2$, 100 µM ATP, 300 µM DTT, and 0.1 mg/mL BSA. A substrate solution containing 20 mM MgCl$_2$, 100 µM ATP, 0.72 µM biotinylated peptide (Biotin-aminohexyl-EEEEYFELVAKKKK-NH$_2$), was added in 5 µL to the assay plate. The solution of activated VEGFR2 was diluted 100-fold in 200 mM HEPES, pH 7.5, 0.2 mg/mL BSA, and 0.6 mM DTT. The VEGFR2 catalyzed reaction was initiated by the addition of 5 µL of the diluted, activated VEGFR2. Final assay concentrations were 100 mM HEPES, pH 7.5, 10 mM MgCl$_2$, 50 µM ATP, 0.1 mg/mL BSA, 300 µM DTT, 0.36 µM biotinylated peptide substrate, and 0.5 nM VEGFR2 (the final assay concentration of VEGFR2 may vary depending on the specific activity of different batches of enzyme). The reaction was run for 90 min. at room temperature and then terminated by the addition of 5 µL of 150 mM EDTA, pH 8. The background signal of the assay was established in wells where the addition of the 150 mM EDTA was instead made prior to adding substrate and enzyme solutions. HTRF detection solution containing 200 mM HEPES, pH 7.5, 0.1 mg/mL BSA, 30 nM Streptavidin SureLight®-APC (PerkinElmer, Boston, Mass., USA), and 4 nM LANCE® europium-labelled antiphosphotyrosine antibody (Perkin Elmer, Boston, Mass., USA) was added in 5 µL. After incubation for 10 min. at room temperature, phosphorylation of the biotinylated peptide substrate was measured as a ratio of specific 665 nm energy transfer signal to reference europium 615 nm signal using a Viewlux 1430 ultraHTS Microplate Imager (PerkinElmer, Turku, Finland).

The compound of formula (I) has an IC$_{50}$ value in this assay of >7.9 µM.

GST-6His-VEGFR2 was overexpressed with N-terminal GST and 6His tags using the baculovirus expression system in Sf9 insect cells. Cells (100-120 grams) were suspended in 50 mM HEPES pH 8.0, 100 mM NaCl, and 20 mM imidazole (5 ml/g cells) at room temperature. All other purification procedures were at 4 C. Cells were lysed with a Branson 450 sonifier (70% power, 50% cycle for one min), and the cell lysate was centrifuged at 30,000×g for 30 min. Supernatant was filtered through a 1.2 µm Pall filter and then loaded (10-20 ml/min) onto a 150 ml Qiagen Ni-NTA (QIAGEN Inc., Valencia, Calif., USA) column equilibrated with 50 mM HEPES pH 8.0, 100 mM NaCl, and 20 mM imidazole. The column was washed with 50 mM HEPES pH 8.0, 100 mM NaCl, and 20 mM imidazole until the absorbance at 280 nm was less than 0.1, then eluted with a 5 column volume gradient from 50 mM HEPES pH 8.0, 100 mM NaCl, 20 mM imidazole to 50 mM HEPES pH 8.0, 100 mM NaCl, 250 mM imidazole. Fractions (10-30 ml) were collected. Desired protein fractions were pooled and loaded (5 ml/min) onto a 25 ml glutathione Sepharose (GE Healthcare, Piscataway, N.J., USA) column equilibrated with 50 mM HEPES pH 7.5, 150 mM NaCl, and 2 mM EDTA. The column was washed with 50 mM HEPES pH 7.5, 150 mM NaCl, and 2 mM EDTA, and protein was eluted with a 3 column volume gradient to 50 mM HEPES pH 7.5, 150 mM NaCl, 1 mM EDTA, and 20 mM glutathione. Fractions are collected, and the desired protein fractions were pooled and concentrated to approximately 20 ml with a Pall JumboSep concentrator with 10,000 MWCO membrane (Pall Corporation, Portsmouth, England). An 1800 ml Superdex S200 or 23 ml G25 (GE Healthcare, Piscataway, N.J., USA) column is equilibrated with 20 mM HEPES pH 7.5, 50 mM NaCl, 0.1 mM EDTA, and 1 mM DTT. The concentrate was loaded onto the column at 8 ml/min., and the column was eluted with 20 mM HEPES pH 7.5, 50 mM NaCl, 0.1 mM EDTA, and 1 mM DTT. Protein fractions (approximately 20 ml) were collected, and the desired fractions are pooled and concentrated with a Pall JumboSep concentrator with 10,000 MWCO membrane. Concentrated protein was stored at −80 C in aliquots of desired volume for later use in the VEGFR2 enzyme activity assay. The identity of GST-6His-VEGFR2 was confirmed by intact liquid chromatography and mass spectrometry (LC/MS) and by proteolytic digestion followed by analysis of the resulting peptides by liquid chromatography and tandem mass spectrometry (LC/MS/MS).

B Cell Activity Assays

4. Ramos pErk Assay

Principle of the Assay

Ramos B cells (human B cells of Burkitt's Lymphoma) are stimulated using anti-IgM. This results in the recruitment of SYK to the B cell receptor. The subsequent autophosphorylation of Syk leads to initiation of a signalling cascade resulting in B cell activation via the Erk MAP Kinase pathway. As a result Erk is phosphorylated and following cell lysis is detected by an immune capture assay.

Stimulation of Ramos Cells with Anti-IqM

Cells were plated at a density of 5×10$^5$/well in a volume of 25 µl assay medium (RPMI containing 10% heat inactivated foetal calf serum, 1% L-glutamine and 1% Penicillin/Streptomycin) in 96 v-well polypropylene plates. 25 µl appropriately diluted compound solution was added and the plate incubated for 30 min at 37° C. with 5% $CO_2$. Cells were stimulated with 5 µl Fab'$_2$ fragments of goat anti-human IgM (5 µg/ml final) for 7 min at 37° C. Cells are lysed by the addition of 55 µL 2×RIPA lysis buffer for 2 h at 4° C.

pErk MSD Assay

50 µl cell lysate was transferred to a 96 well MSD plate coated with anti-pErk1/2 (Thr/Thy: 202/204; 185/187) capture antibody and incubated for 16 hours at 4° C. The plate was washed and an anti-pErk detection antibody added (25 µl/well) for 2 h at room temperature. This was removed, 150 µL MSD read buffer added and the resultant electrochemiluminescence signal measured.

The compound of formula (I) has an $IC_{50}$ value in this assay of 50 nM.

Compound Preparation

Compound was prepared as a 10 mM stock in DMSO and a dilution series prepared in DMSO using 9 successive 5-fold dilutions. This dilution series was diluted a further 1:100 with assay medium to give the concentration range to be tested of $5 \times 10^{-5}$ to $2.56 \times 10^{-11}$ M. Compound dilutions were prepared using the Biomek 2000 and Biomek Nx automated robotic pipetting systems.

5. CD69 PBMC Assay

Principle of the Assay

Peripheral blood B cells are stimulated ex-vivo using anti-IgM. This results in the recruitment of Syk to the B cell receptor. The subsequent autophosphorylation of Syk leads to initiation of a signalling cascade resulting in B cell activation as indicated by expression of the activation marker CD69 on the cell surface. CD20/CD69+ve whole blood B cells are detected by flow cytometry.

Stimulation of Peripheral Blood B Cells with Anti-IqM

Peripheral blood B cells were prepared from heparinised human blood by density gradient centrifugation. Cells were plated at a density of $1 \times 10^5$/well in a volume of 25 µl assay medium (RPMI containing 10% heat inactivated foetal calf serum, 1% L-glutamine and 1% Penicillin/Streptomycin) in 96 v-well polypropylene plates. 25 µl appropriately diluted compound solution was added and the plate incubated for 30 min at 37° C. with 5% $CO_2$. Cells were stimulated with 5 µl Fab'$_2$ fragments of goat anti-human IgM (5 µg/ml final) for a further 3.5 h under the conditions previously described. Any red blood cells present were lysed, and all other cells fixed, by the addition of 200 µl Lyse/Fix buffer for 10 min at room temperature.

CD69 Assay

The cells were stained using a cocktail of mouse anti-human CD20 FITC and mouse anti-human CD69 APC conjugated antibodies. CD20/CD69+ve B cells present in the sample were detected by flow cytometry.

Compound Preparation

Compound was prepared as a 10 mM stock in DMSO and a dilution series prepared in DMSO using 9 successive 5-fold dilutions. This dilution series was diluted a further 1:100 with assay medium to give the concentration range to be tested of $5 \times 10^{-5}$ to $2.56 \times 10^{-11}$ M. Compound dilutions were prepared using the Biomek 2000 and Biomek Nx automated robotic pipetting systems.

6. CD69 Whole Blood Assay

Principle of the Assay

Whole blood B cells are stimulated ex-vivo using anti-IgM. This results in the recruitment of Syk to the B cell receptor. The subsequent autophosphorylation of Syk leads to initiation of a signalling cascade resulting in B cell activation as indicated by expression of the activation marker CD69 on the cell surface. CD20/CD69+ve whole blood B cells are detected by flow cytometry.

Stimulation of Whole Blood B Cells with Anti-IqM

100 µl heparinised human blood was added to a 5 ml polypropylene tube containing 1 µl appropriately diluted compound solution and incubated for 30 min at 37° C. with 5% $CO_2$. B cells were stimulated with 10 µl Fab'$_2$ fragments of goat anti-human IgM (67.5 µg/ml final) for a further 3.5 h under the conditions previously described. The red blood cells were lysed and all other cells fixed by the addition of 2 ml Lyse/Fix buffer for 10 min at room temperature.

CD69 Assay

The cells were stained using a cocktail of mouse anti-human CD20 FITC and mouse anti-human CD69 APC conjugated antibodies. CD20/CD69+ve B cells present in the sample were detected by flow cytometry.

Compound Preparation

Compound was prepared as a 10 mM stock in DMSO and a dilution series prepared in DMSO using 7 successive 3-fold dilutions to give the concentration range to be tested of $1 \times 10^{-5}$ to $4.5 \times 10^{-10}$ M. Compound dilutions were prepared using the Biomek 2000 automated robotic pipetting system.

Mast Cell Activity

7. LAD2 Assay

Principle of the Assay

LAD2 is a stem cell factor (SCF)-dependent human mast cell line that was established by the NIH from bone marrow aspirates from a patient with mast cell sarcoma/leukaemia. LAD2 cells resemble CD34+-derived human mast cells and express functional FcεRI. The FcεRI is up-regulated in the presence of IL-4, SCF and IgE, subsequent cross linking of cell-bound IgE results in degranulation which can be measured as hexosaminidase release.

Priming LAD2 Cells to Up-Requlate FcεRI

LAD2 cells are re-suspended at $1 \times 10^5$/ml in complete stem pro-34SFM (Gibco Cat 10640-019 media containing Stem Pro-34 nutrient supplement (1:40), glutamine (2 mM), penicillin (100 µg/ml), streptomycin (100 µg/ml)) with additional supplements of human recombinant SCF (100 ng/ml; R&D systems), human recombinant Interleukin-4 (6 ng/ml; R&D Systems) and IgE (100 µg/ml; Calbiochem). Cells are then maintained for 5 days at 37° C., 5% CO2 in a humidified atmosphere.

Compound Preparation

Compounds are titrated from a 2 mM stock in 100% DMSO to give 9 successive 1:3 dilutions (V 96-well Nunc; Biomek 2000). From this master plate 3 µl is dispensed into a daughter plate (flat 96-well NuncBiomek Fx) which is then diluted 1:40 in RPMI with 2 mM glutamine, and 20 µl of the diluted compound transferred into the Greiner cell plate.

Therefore the final compound concentration range is $1\times10^{-5}$M to $5\times10^{-10}$M in a constant 0.5% DMSO. Control wells are treated with 0.5% DMSO.

Activation of LAD2 Cells with Anti-IqE

Primed LAD2 cells are centrifuged (400 g, 5 min), the supernatant discarded and the cell pellet re-suspended at $1\times10^4$ cells/ml in RPMI supplemented with glutamine (2 mM). Following a further centrifugation (400 g, 5 min) the cells are re-suspended in fresh RPMI with glutamine (2 mM), adjusted to a density of $5.7\times10^5$/ml, and pipetted into sterile V-well plates (70 μl/well; Greiner) containing 20 μl diluted compound (prepared as detailed above). Cells are then incubated for 1 h (37° C., 5% $CO_2$ in a humidified atmosphere) before activating with a sub-maximal concentration of anti-IgE (10 μl volume to give a final assay dilution of 1:2700; Sigma). Following a 40 min incubation (37° C., 5% $CO_2$ in a humidified atmosphere), plates are centrifuged (1200 g, 10 min, 4° C.) and the supernatant removed for hexosaminidase assay. The cell pellet is lysed in 100 μl/well triton-X (0.5% in RPMI 2 mM glutamine) at 37° C. for 30 min.

Beta-hexosaminidase Assay

Beta-hexosaminidase activity is measured by the conversion of 4-methylumbelliferyl N-acetyl-ε-D glucosaminide (Sigma) to a fluorescent product.

Supernatant or lysate (25 μl) is incubated with an equal volume of 4-methylumbelliferyl N-acetyl-ε-D glucosaminide (500 μM in 0.2M sodium citrate buffer, pH 4.5) in black 96-well plate (Nunc) for 1 h at 37° C. The reaction is then terminated by addition of Trizma pH9 (90μl) and the fluorescent product measured using excitation 356 nm and emission 450 nm (Tecan Safire)

hERG Activity

8. Cy3B Dofetilide Fluoro-ligand Binding Assay for hERG

Compound potencies were determined by a fluoro-ligand (Cy3b-Dofetilide) fluorescence polarisation assay.

hERG-expressing CHO-K1 membranes* (60 μg/ml) were incubated with 1.0 nM fluoro-ligand[§], in assay buffer (25 mM HEPES, 1.2 mM $MgCl_2$, 100 mM KCl and 0.1% pluronic, pH adjusted to 7.4 using 5M KOH). The final potassium concentration in the assay was 100 mM. After 70 min mixing at room temperature, in the dark, 10 μl was dispensed into each well of a black LV Greiner 384-well plate containing 0.1 μl of test compound in DMSO. The plates were left to equilibrate for 2 h before reading on an Acquest™/Analyst™ imager. $pIC_{50}$ data were generated using from an 11-point inhibition curve (top assay concentration of 50 μM and a 1:3 step-dilution), a six parameter curve-fit being applied using ABase and $IC_{50}$ to analyse data and generate curve fits.

*CHO-K1 membranes
[§]Fluoro-ligand (octahydrobenzo[2",3"]indolizino[8",7":5',6']pyrano[3',2':3,4]pyrido[1,2-a]indol-5-ium-2-sulfonate The compound of formula (I) has an $IC_{50}$ value in this assay of 25 μM.

Chinese Hamster Ovary (CHO) cells stably expressing the human hERG receptor were grown to 80% confluency before being harvested by trypsinisation and subsequent centrifugation at 500 g for 10 min. Cell pellets were frozen at −80 C before membrane production. The frozen pellet was thawed on ice, re-suspended and homogenised in 10 volumes of membrane buffer (50 mM HEPES, pH 7.4, 1 mM EDTA, 1 mM PMSF, $2\times10$–6M Pepstatin A). The membrane suspension was centrifuged for 20 min at 500 g, the pellet discarded and the supernatant spun again at 48,000 g for 30 min. Following the second centrifugation the remaining pellet containing the membrane fraction was re-suspended in an appropriate volume (4 ml for each ml of frozen cell pellet) and assayed for protein concentration.

TFA salt described in J.M.C. 2007, 50(13), 2931-2941.

N-[4-({2-[(6-aminohexyl)(2-{4-[(methylsulfonyl)amino]phenyl}ethyl)amino]ethyl}oxy)phenyl]methanesulfonamide (1.508 mg) as a solution in acetonitrile (100 μl) was added to solid Cy3B-ONSu (14-{2-[(2,5-dioxo-1-pyrrolidinyl)oxy]-2-oxoethyl}-16,16,18,18-tetramethyl-6,7,7a,8a,9,10,16,18-octahydrobenzo[2",3"]indolizino[8",7":5',6']pyrano[3',2':3,4]pyrido[1,2-a]indol-5-ium-2-sulfonate (1.7 mg, WO9931181) in a silanised 4 ml vial. A second portion of acetonitrile (100 μl) was added followed by Hunig's base (0.9 μl). Two portions (2×50 μl) of dimethylformamide were added and the reaction mixture was concentrated under reduced pressure. The residue was re-dissolved in dimethylformamide (200 μl). Hunig's base (0.9 μl) was added and the mixture vortex mixed for 22 h. The reaction mixture was evaporated to dryness, re-dissolved in acetonitrile/water/acetic acid (5/4/1, ~500μl), filtered and applied to a semi-preparative Spherisorb ODS2 HPLC column which was eluted with the following gradient (flow rate=5 ml/min, AU 5.0, 214 nm, AU 2, 256 nm, A=0.1%TFA/water, B=90% acetonitrile/10% water/0.1% TFA): t=0 min: B=5%; t=10 min: B=5%; t=30 min: B=25%; t=90 min: B=55%; t=105 min: B=100%; t=120 min: B=100%. The major component eluted between 46% and 48%B and collected in one fraction which was evaporated to dryness and the purple solid transferred to a vial using methanol as solvent. The methanol was removed under reduced pressure and the purple solid triturated with dry ether. The solid was dried overnight at 1 mbar in a drying pistol to give the title compound (1.2 mg).

N-[4-({2-[(6-aminohexyl)(2-{4-[(methylsulfonyl)amino]phenyl}ethylamino]ethyl}oxy)phenyl]methanesulfonamide Crude N-[4-({2-[[6-(1,3-dioxo-1,3-dihydro-2H-isoindol-2-yl)hexyl](2-{4-[(methylsulfonyl)amino]phenyl}ethyl)amino]ethyl}oxy)phenyl]methanesulfonamide (142 mg) was dissolved in methylamine (33% in ethanol, 10 ml, 0.216) and left at 22° C. for 48 h. Excess reagent was evaporated under reduced pressure and the oily residue azeotroped with two further portions of ethanol. The crude product was dissolved in acetonitrile/water/acetic acid (5/4/, <2 ml), half applied to a Phenomenex Jupiter C18 HPLC column and eluted using the following gradient (flow rate=10 ml/min, AU 20.0, 214 nm, AU 10, 256 nm, A=0.1%TFA/water, B=90% acetonitrile/10% water/0.1% TFA): t=0 min: B=5%; t=10 min: B=5%; t=100 min: B=35%; t=115 min: B=100%; t=130 min: B=100%. Fractions containing mainly the slower eluting component (>90%) were pooled and evaporated to give the title compound (14.9 mg). The remaining crude was applied to the C18 column but with a modified gradient: t=0 min: B=5%; t=10 min: B=5%; t=15 min: B=10%; t=95 min: B=30%; t=110 min: B=100%; t=125 min: B=100%. Fractions containing mainly the desired product were combined and evaporated as before to yield the title compound (21.3 mg~80% purity). The material was used without further purification.

N-[-4-({2-[[6-(1,3-dioxo-1,3-dihydro-2H-isoindol-2-yl]hexyl](2-{4-[(methylsulfonyl)amino]phenyl}ethyl)amino]ethyl}oxy)phenyl]methanesulfonamide 2-[6-([2-(4-aminophenypethyl]{2-[(4-aminophenyl)oxy]ethyl}amino)hexyl]-1H-isoindole-1,3(2H)-dione (108.3 mg)

was dissolved in DCM (5 ml) and cooled to 0-4° C. in an ice-bath. Hunig's Base (0.227 ml) was added followed by the dropwise addition of mesylchloride (0.051 ml). The reaction was maintained at 0-4° C. for 0.5 h and then allowed to warm slowly to room temperature. After 3 h the reaction mixture was evaporated to dryness and used crude in next step.

2-[6-([2-(4-aminophenyl)ethyl]{2-[(4-aminophenyl)oxy]ethyl}amino)hexyl]-1H-isoindole-1,3(2H)-dione 2-[6-([2-(4-nitrophenypethyl]{2-[(4-nitrophenyl)oxy]ethyl}amino)hexyl]-1H-isoindole-1,3(2H)-dione (0.35 g) was dissolved in a mixture of ethanol (40 ml), water (5 ml) and acetic acid (5 ml) and the resulting solution degassed under reduced pressure. 10% Palladium on carbon (56% paste, 0.27 g) was added and the resulting mixture stirred vigorously under a hydrogen atmosphere (atmospheric pressure) for 12 h. The reaction mixture was filtered through Celite™ and washed with ethanol. The filtrate and washings were evaporated to dryness to give the title compound (0.313 g) which was used without further purification.

2-[6-([2-(4-nitroohenyl)ethyl]{2-[(4-nitrophenyl)oxy]ethyl}amino)hexyl]-1H-isoindole-1,3(2H)-dione

[2-(4-Nitrophenyl)ethyl]{2-[(4-nitrophenyl)oxy]ethyl}amine (253 mg) and 2-(6-bromohexyl)-1H-isoindole-1,3(2H)-dione (1186 mg) were dissolved in DMF (4 ml) and basified by the addition of DIPEA (0.665 ml). The reaction was stirred for 120 h. The reaction mixture was evaporated to dryness and the residue dissolved in DCM, the solution was absorbed onto a pad of silica and purified on a silica cartridge (12 g) eluting with the following gradient: (A=DCM, B=methanol) t=0 min: B=10%; t=7.5 min: B=0%; t=22.5 min: B=5%. The desired product eluted at ~15%B (isocratically) and evaporation of the solution to dryness gave the title compound (0.364 g).

[2-(4-nitroohenyl)ethyl]{2-[(4-nitroohenyl)oxy]ethyl}amine

[[2-(4-nitrophenyl)ethyl]amine (498.9 mg) and 111-[(2-bromoethyl)oxy]-4-nitrobenzene 2-bromoethyl 4-nitrophenyl ether (513 mg) were dissolved in DMF (5 ml) at 22° C. and DIPEA (0.872 ml) added. The reaction mixture was left for 60 h at 22° C., evaporated to dryness and the residue dissolved in DCM. The compound was absorbed onto silica and purified on a silica cartridge (12 g) in two batches eluting with a methanol/DCM gradient (0-15%). Fractions containing pure product were pooled and the solvent removed under reduced pressure. The resulting title compound was isolated as a deep yellow oil which partially solidified under high vacuum (253 mg).

Results

|  | Example 1 | | | Reference example 1 | | |
| --- | --- | --- | --- | --- | --- | --- |
|  | pIC50 | n | IC50 | pIC50 | n | IC50 |
| Syk enzyme assay (1) | 7.4 | 7 | 40 nM | 8.2 | 146 | 6.3 nM |
| RAMOS pErk assay (4) | 7.3 | 6 | 50 nM | 7.5 | 74 | 32 nM |
| CD69 whole blood assay (6) | <6.3 (6.5)* | 16 (14)* | 500 nM (320 nM)* | 6.3 | 73 | 500 nM |
| hERG activity assay (8) | 4.6 | 2 | 25 uM | 5.4 | 47 | 4.0 uM |
| Aurora B enzyme assay (2) | 4.7 | 3 | 20 uM | 5.8 | 111 | 1.6 uM |
| Vegfr enzyme assay (3) | <5.1 | 2 | >7.9 uM | 5.2 | 3 | 6.3 uM |

*2 outlying data points at <5 and 5.2, excluded from data in brackets

Reference example 1 is the compound:

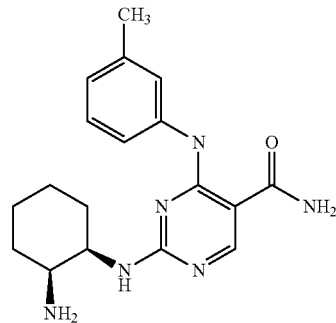 [SMILES: Cc1cccc(Nc2nc(N[C@@H]3CCCC[C@@H]3N)ncc2C(N)=O)c1]

which is described in WO9903101073 (Yamanouchi Pharmaceutical Co Ltd), as example 35, as the racemic mixture.

INTERMEDIATES AND EXAMPLES

General
All temperatures are in ° C.
DBU refers to 1,8-diazabicyclo[5.4.0]undec-7-ene
DCM refers to dichloromethane
DMSO refers to dimethylsulfoxide.
DMF refers to N,N-dimethylformamide
dppf refers to 1,1'-bis(diphenylphosphino)ferrocene
Ether refers to diethyl ether
HPLC refers to high performance liquid chromatography
IPA refers to propan-2-ol
mCPBA refers to m-chloroperbenzoic acid
r.t. refers to room temperature
TBME refers to t-butylmethylether
THF refers to tetrahydrofuran
$^1$H NMR spectra were recorded using a Bruker DPX 400 MHz, referenced to tetramethylsilane.
LC/MS (Method A) was conducted on an Acquity UPLC BEH C18 column (50 mm×2.1 mm i.d. 1.7 µm packing diameter) at 40 degrees centigrade, eluting with 10 mM Ammonium Bicarbonate in water adjusted to pH 10 with Ammonia solution (Solvent A) and Acetonitrile (Solvent B) using the following elution gradient 0-1.5 min 1-97% B, 1.5-1.9 min 97% B, 1.9-2.0 min 100% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

LC/MS (Method B) was conducted on an Acquity UPLC BEH C18 column (50 mm×2.1 mm i.d. 1.7 μm packing diameter) at 40 degrees centigrade, eluting with 0.1% v/v solution of Formic Acid in Water (Solvent A) and 0.1% v/v solution of Formic Acid in Acetonitrile (Solvent B) using the following elution gradient 0-1.5 min 3-100% B, 1.5-1.9 min 100% B, 1.9-2.0 min 3% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

Silica chromatography techniques include either automated (Flashmaster) techniques or manual chromatography on pre-packed cartridges (SPE) or manually-packed flash columns.

When the name of a commercial supplier is given after the name of a compound or a reagent, for instance "compound X (Aldrich)" or "compound X/Aldrich", this means that compound X is obtainable from a commercial supplier, such as the commercial supplier named.

Similarly, when a literature or a patent reference is given after the name of a compound, for instance compound Y (EP 0 123 456), this means that the preparation of the compound is described in the named reference.

The names of the above mentioned Examples have been obtained using the compound naming programme "ACD Name Pro 6.02".

Compounds of the present invention have the (3R,4R) absolute stereochemistry.

2,4-dichloro-5-pyrimidinecarbonyl chloride

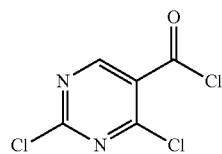 [SMILES: O=C(Cl)c1cnc(Cl)nc1Cl]

A solution of 2,4-dihydroxy-pyrimidine-5-carboxylic acid (50 g) and phosphorous pentachloride (239 g) in phosphorous oxychloride (230 ml) was stirred at 115° C. overnight. The excess phosphorous oxychloride was removed in vacuo and ethyl acetate (200 ml) added to the residue. The mixture was filtered and the filtrate was concentrated to give yellow oil (78 g) as crude 2,4-dichloro-5-pyrimidinecarbonyl chloride which was used in the next step without further purification.

1H NMR (300 MHz, D$_6$-DMSO): δH 9.13 (1H, s).

2,4-dichloro-5-pyrimidinecarboxamide

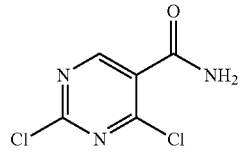

A solution of ammonia (14 g) in 1,4-dioxane (500 ml) was added drop-wise to an ice-cooled stirred solution of 2,4-dichloro-5-pyrimidinecarbonyl chloride (78 g, crude) in 1,4-dioxane (400 ml) under nitrogen. The ice-bath was removed and the solution was stirred for 30 min and concentrated. The solid residue was partitioned between ethyl acetate (500 ml) and saturated aqueous sodium bicarbonate (500 ml), the organic washed with saturated aqueous sodium bicarbonate (500 ml, ×2), followed by brine (300 ml). The organic phase was dried (sodium sulphate) and concentrated to give a yellow solid. To the residue was added diethyl ether (50 ml) and the resulting suspension was treated under ultrasonic wave for 8 min then filtered. The residue was washed with ethyl ether (50 ml) to give the title compound as a white solid (30 g).

MS: MH$^+$ 192

1H NMR (400 MHz, D$_6$-DMSO): δH 8.90(1H, s), 8.19 (1H, s), 8.07 (1H, s).

2-chloro-4-[(4-methylphenyl)amino]-5-pyrimidinecarboxamide

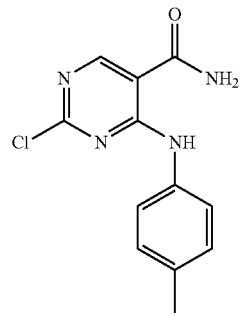 [SMILES: Cc1ccc(Nc2nc(Cl)ncc2C(N)=O)cc1]

A solution of p-toluidine (46.9 g) in DMF (100 ml) was added dropwise to a solution of 2,4-dichloro-5-pyrimidinecarboxamide (80 g) and triethylamine (63.9 ml) in DMF (300 ml) with ice cooling. The mixture was stirred for 2 h allowing to warm to room temperature, then added to water (1 l) and stirred for 20 min. The slurry was filtered and the solid washed with water. The solid was suspended in a mixture of methanol (500 ml) and ether (500 ml), stirred for 20 min and filtered to give 2-chloro-4-[(4-methylphenyl)amino]-5-pyrimidinecarboxamide as pale yellow solid (94.2 g).

LCMS (Method B): Rt 1.02 min, MH$^+$ 263/265.

1H NMR (400 MHz, MeOD): δH 8.63(1H, s), 7.53(2H, d), 7.18(2H, d), 2.33(3H, s).

3,6-dihydro-2H-pyran

Sodium hydroxide (10N, 1745 ml) was added to 4-bromotetrahydro-2H-pyran (1133.7 g), the mixture warmed to 90° C. with stirring and stirred at ~90° C. for 27 h. The mixture was allowed to cool to ambient temperature, 1800 ml of the aqueous phase was separated and the bulk of the organic phase collected. The remaining aqueous phase plus a small volume of the organic phase and the interfacial material was washed with water (20 ml), filtered and the filtrate washed with sodium hydroxide solution (10N, 5 ml). The organic phase was separated and added to the bulk of material to give 3,6-dihydro-2H-pyran (242.2 g).

1H NMR (400 MHz, CDCl$_3$): δH 5.85 (1H, m), 5.72 (1H, d), 4.13(2H, m), 3.79(2H, t), 2.14(2H, m).

3,6-dihydro-2H-pyran

Tetrahydro-4-pyranol (1005.2 g), DCM (5530 ml) and triethylamine (1640 ml) were combined and cooled to 1° C. Mesyl chloride (1243.8 g) was added to the cooled and stirred mixture in a controlled manner over ~2.5 h maintaining the temperature below 15° C. The mesyl chloride was washed in with DCM (500 ml) and the reaction allowed to warm to ambient temperature overnight. The mixture was treated with aqueous ammonium chloride (~2 l, 9.8% w/w), stirred for 5 min and the phases separated. The organic phase was washed with aqueous ammonium chloride (~2 l, 9.8% w/w), water (~2 l) and dried (sodium sulphate). The organic phase was concentrated in vacuo (39° C., ~15 mbar) to an oil which rapidly solidified on standing (1733.9 g). This material was treated slowly with DBU (~300 ml) at 52° C., over 30 min a solution formed and this was treated with DBU (1.7 l) and the mixture warmed to ~100° C. (external temperature) over 1 h and maintained at this temperature for 2 h. The temperature was raised slowly to 148° C. (external) and the distilling 3,6-dihydro-2H-pyran collected (527.5 g).

1H NMR (400 MHz, CDCl$_3$): δH 5.85 (1H, m), 5.72 (1H, d), 4.13(2H, m), 3.79(2H, t), 2.14(2H, m).

1,5:3,4-dianhydro-2-deoxypentitol

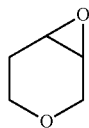

To a suspension of mCPBA (71.1%, 1524.2 g) in chloroform (4.22 l) at 13° C. was added 3,6-dihydro-2H-pyran (526.5 g) over ~2 h washing solid down from vessel neck at intervals with portions of chloroform (total ~1.5 l). A further portion of chloroform (0.5 l) was added and the reaction mixture stirred at 15° C. for 2.25 h. The reaction mixture was warmed to 20° C. over 40 min and stirred at 20° C. overnight. The reaction mixture was cooled to 0° C., filtered and the solid washed with chilled chloroform (3.5° C., 1055 ml). The combined filtrate and washings were washed with aqueous sodium carbonate (20% w/w, 1582 ml), the phases separated and the organic phase treated with sodium sulphite (1 kg). The organic was filtered and concentrated in vacuo (25° C., 150 mbar) to give the title compound (506 g). The solvent from the in vacuo concentration was re-concentrated in vacuo to yield a second portion of the title compound (41.2 g).

1H NMR (400 MHz, D$_6$-DMSO): δH 3.91(1H, d), 3.77 (1H, d), 3.35-3.29(3H, m partially obscured by water), 3.15 (1H, s), 1.87(2H, m).

1,5-anhydro-2,4-dideoxy-2-{[(1S)-1-phenylethyl]amino}-L-threo-pentitol

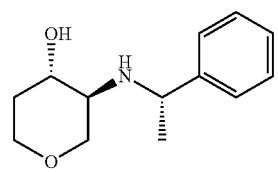 [SMILES: C[C@H](N[C@H]1COCC[C@@H]1O)c1ccccc1]

Method 1

1,5:3,4-Dianhydro-2-deoxypentitol (589.2 g, 92.7% w/w) was added to [(1S)-1-phenylethyl]amine (660 g) and isopropanol (500 ml). Further isopropanol (2800 ml) was added, the mixture warmed to 69° C. and maintained at this temperature for 96 h. The solvent was evaporated in vacuo and the crude product slurried with TBME (2640 ml). The mixture was filtered, the residue washed with TBME (660 ml), TBME/heptane (1:1, 660 ml), and heptane (2×1320 ml) and dried at 40° C. in vacuo overnight to give the title compound (297.5 g). The TBME and TBME/heptane washings were combined and reduced to dryness under vacuum. The residue was dissolved in TBME (990 ml) with warming, the solution cooled to 32° C. and rotated overnight. The solid was isolated by filtration, washed with TBME (130 ml), TBME/heptane (1:1, 130 ml), and heptane (2×260 ml). The solid was dried at 40° C. in vacuo overnight to give a second crop of the title compound (58.69 g).

1H NMR (400 MHz, D$_6$-DMSO): δH 7.34-7.27(4H, m), 7.19(1H, t), 4.87(1H, d), 3.88(1H, m), 3.67(1H, m), 3.35-3.30 (2H, m, partially obscured by water), 3.20(1H, t), 2.70(1H, t), 2.25(1H, m), 1.92(1H, s), 1.76(1H, dd), 1.38(1H, m), 1.24 (3H, d).

Method 2

2-butanol (1.5 ml) was added to a mixture of 1,5:3,4-dianhydro-2-deoxypentitol (1.68 g, 90.4% w/w) and [(1S)-1-phenylethyl]amine (2.02 g) and the reaction heated at 90° C. under nitrogen for 20 h. The reaction was cooled to 72° C. and heptane (13.5 ml) added dropwise over 30 min to the reaction mixture. The heating was stopped and the reaction allowed to cool to 34° C., as no solid was produced the reaction was rewarmed to 40° C., and seeded with 1,5-anhydro-2,4-dideoxy-2-{[(1S)-1-phenylethyl]amino}-L-threo-pentitol. The resulting suspension was stirred at 35° C. for 30 min, allowed to cool to 23° C. over 30 min and then left at this temperature for 2 h 25 min. The solid was collected by filtration, washed with 2-butanol/heptane (10% v/v, 3 ml) and then with heptane (2×6 ml). The solid was dried in vacuo at 35° C. to give the title compound (1.10 g).

1H NMR (400 MHz, D$_6$-DMSO): δH 0.34-7.27(4H, m), 7.20(1H, t), 4.92(1H, d), 3.88(1H, m), 3.67(1H, m), 3.36-3.29

(2H, m, partially obscured by water), 3.19(1H, t), 2.69(1H, t), 2.24(1H, m), 1.94(1H, s), 1.76(1H, dd), 1.36(1H, m), 1.23 (3H, d).

1,5-anhydro-2,4-dideoxy-2-{[(1R)-1-phenylethyl]amino}-L-threo-pentitol

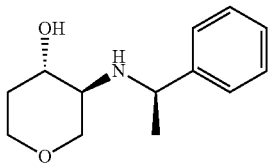 [SMILES: C[C@@H](N[C@H]1COCC[C@@H]1O)c1ccccc1]

To a solution of [(1R)-1-phenylethyl]amine (3.5 ml) in DCM (20 ml) stirred under nitrogen at −5 to 0° C. was added a solution of trimethyl aluminium (14.6 ml) in toluene portionwise over 30 min. The reaction mixture was stirred at <0° C. for 40 min and then a solution of pyran epoxide (7.7 g) in DCM (20 ml) was added over 10 min. Stirring was continued with ice cooling for 5 h and the reaction allowed to warm over 15 h. The mixture was cooled in ice to 2.5° C. and sodium fluoride (5 g) was added followed by water (3.2 ml) causing the temp to rise to 28° C. and then fall to 5° C. in 15 min. The ice bath was removed and stirring continued for 1 h. The mixture was filtered through a pad of Celite, the Celite washed with DCM (3×~30 ml). The 3rd wash was discarded, but the remainder of the filtrate was concentrated to give a colourless oil (6.05 g) which crystallised to a waxy solid. The waxy solid (5.94 g) was triturated with ether (10 ml) and left for 1 h. The resulting white solid was filtered off, washed with 40-60 petrol and the residue triturated further with 40-60 petrol. The filtrate was evaporated to give a gum (3.04 g) to which was added 40-60 petrol (25 ml) the mixture swirled around and left for 1 h. The petrol was decanted and set aside. Crystals formed and were filtered off after 3 days giving 1,5-anhydro-2,4-dideoxy-2-{[(1R)-1-phenylethyl]amino}-L-threo-pentitol (104 mg).

1H NMR (400 MHz, $D_6$-DMSO): δH 7.34-7.28(4H, m), 7.21(1H, m), 4.80(1H, d), 3.87(1H, dd), 3.78(1H, m), 3.70 (1H, m), 3.31-3.22 (2H, m, partially obscured by water) 2.92 (1H, m), 2.21(1H, m), 2.06(1H, m), 1.72(1H, m), 1.32-1.20 (4H, m).

2-amino-1,5-anhydro-2,4-dideoxy-L-threo-pentitol

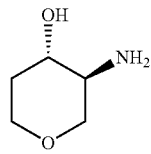

Method 1

A mixture of 1,5-anhydro-2,4-dideoxy-2-{[(1S)-1-phenylethyl]amino}-L-threo-pentitol (348.6 g) and palladium hydroxide on charcoal (20% w/w, wet with ca. 50% water, 35 g) were suspended in ethanol (5230 ml). The reaction vessel was charged with hydrogen (15 psi) and vented (×2), and then the mixture hydrogenated under 15 psi of hydrogen at ca 25° C. overnight. The vessel was purged with nitrogen (×8), then with hydrogen (×1) and hydrogenation under 15 psi of hydrogen continued for ~5 h. The vessel was purged with nitrogen (×5), then hydrogen (×1) and hydrogenation under 15 psi of hydrogen continued for ~15 h. The reaction was filtered through Celite and then through a 1 micron Dominick Hunter before evaporation of the solvent in vacuo. The residue was dissolved in methanol with warming, filtered through Celite, then through a 0.2 micron Dominick Hunter before evaporation of the solvent in vacuo to leave the title compound. This material was used without further purification.

1H NMR (400 MHz, $D_6$-DMSO includes): δH 3.76(1H, d), 3.69(1H, dd), 3.26(1H, t), 3.14(1H, m), 2.85(1H, t), 2.39(1H, m), 1.74(1H, dd), 1.36(1H, m).

Method 2

A solution of 1,5-anhydro-2,4-dideoxy-2-{[(1S)-1-phenylethyl]amino}-L-threo-pentitol (25.5 g) in ethanol (500 ml) was hydrogenated (1 Atm) over 20% palladium hydroxide on carbon (2.5 g) for 18 h at room temp. The catalyst was filtered off through a Celite cartridge (10 g) and the filtrate was reduced to dryness under vacuum to give the title compound (13.26 g).

1H NMR (400 MHz, $D_6$-DMSO): δH 3.74(1H, m), 3.67 (1H, m), 3.24,(1H, m), 3.13(1H, m), 2.84(1H, m), 2.38(1H, m), 1.72(1H, m), 1.34(1H, m).

Rotation: +34.2°, c=1 in methanol at 24° C.

Method 3

1,5-Anhydro-2,4-dideoxy-2-{[(1R)-1-phenylethyl]amino}-L-threo-pentitol (80 mg) was dissolved in methanol (8 ml). The reaction was hydrogenated using H-cube™ flow hydrogenation (settings: 50° C., 50 bar, 1 ml/min flow rate) over Palladium hydroxide on Carbon (20%,CatCart 30). The resulting solution was reduced to dryness under a stream of nitrogen and the resulting white solid dried in vacuo to give 2-amino-1,5-anhydro-2,4-dideoxy-L-threo-pentitol (21 mg).

1H NMR (400 MHz, $D_6$-DMSO includes): δH 3.76(1H, m), 3.69(1H, m), 3.26(1H, m), 3.15(1H, m), 2.85(1H, m), 2.40(1H, m), 1.74(1H, m), 1.35(1H, m).

Rotation: +31°, c=1.016 in methanol at 25.2° C.

1,5-anhydro-2,4-dideoxy-2-({[(1,1-dimethylethyl)oxy]carbonyl}amino)-L-threopentitol

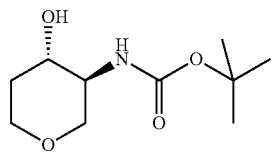

Method 1

2-amino-1,5-anhydro-2,4-dideoxy-L-threo-pentitol (~184 g) in methanol (1300 ml) was treated with triethylamine (22 ml). Bis(1,1-dimethylethyl) dicarbonate (369 g) was dissolved in methanol (530 ml) was added to the mixture over 35 min and washed in with methanol (30 ml). The reaction was stirred at 20° C. for ~21.5 h and concentrated under reduced pressure. TBME (280 ml) and cyclohexane (2520 ml) were added to the residue and the mixture rotated at 20° C. for ~2.5 h. The resulting solid was isolated by filtration and washed with cyclohexane (2×780 ml). The solid was dried at 30-35° C. under vacuum to give the title compound as a white solid (325.76 g).

1H NMR (400 MHz, $D_6$-DMSO): δH 6.60(1H, bd), 4.77 (1H, d), 3.72(2H, m), 3.39(1H, m), 3.26-3.11(2H, m), 2.89 (1H, t), 1.82(1H, m), 1.38(10H, m).

Method 2

2-Amino-1,5-anhydro-2,4-dideoxy-L-threo-pentitol (13.2 g) was suspended in TBME (220 ml). Triethylamine (1.57 ml) and bis(1,1-dimethylethyl) dicarbonate (29.5 g) were added and the mixture heated at reflux overnight. Cyclohexane (220 ml) was added to the reaction, raising the bath temperature to 85° C. to keep the mixture at reflux. The reaction mixture was allowed to cool slowly to room temperature over 3 h and then kept in the fridge for 2 h. The crystals were filtered off, washed with cold cyclohexane/TBME (1:1, 25 ml), cyclohexane (25 ml) and dried under reduced pressure at 40° C. to give the title compound (16.44 g). A second crop of the title compound was obtained from the filtrate (0.495 g)

1H NMR (400 MHz, $D_6$-DMSO): δH 6.64(1H, d), 4.79 (1H, d), 3.75(1H, m), 3.69(1H, dd), 3.38(1H, m), 3.26-3.12 (2H, m), 2.88(1H, m), 1.82(1H, m), 1.44-1.35(10H, m). Rotation: +31.3°, c=1 in methanol at 23.7° C.

1,5-anhydro-2,4-dideoxy-2-({[(1,1-dimethylethyl)oxy]carbonyl}amino)-3-O-(methylsulfonyl)-L-threo-pentitol

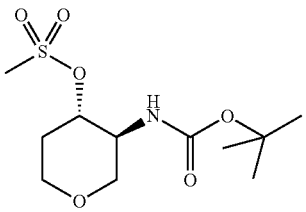 [SMILES: CC(C)(C)OC(=O)N[C@H]1COCC[C@@H]1OS(C)(=O)=O]

Methanesulfonyl chloride (30 ml) in DCM (100 ml) was added dropwise to a solution of 1,5-an hydro-2,4-dideoxy-2-({[(1,1-dimethylethyl)oxy]carbonyl}amino)-L-threo-pentitol (75 g) and triethylamine (58 ml) in DCM (900 ml) at 0° C., maintaining the temperature below 3° C. during the addition. The mixture was stirred for 30 min, warmed to 25° C. and stirred for 2 h. The reaction mixture was washed with water (2×1.4 l), the organic phase dried and the solvent evaporated to give 1,5-anhydro-2,4-dideoxy-2-({[(1,1-dimethylethy)oxy]carbonyl}amino)-3-O-(methylsulfonyl)-L-threo-pentitol (103.1 g).

1H NMR (400 MHz, $CDCl_3$): δH 5.02(1H, bd), 4.75(1H, m), 4.01(1H, dd), 3.87(1H, m), 3.70-3.57(2H, m), 3.46(1H, m), 3.10(3H, s), 2.20(1H, m), 1.93(1H, m), 1.45(9H, s).

1,1-dimethylethyl [(3R,4R)-4-azidotetrahydro-2H-pyran-3-yl]carbamate

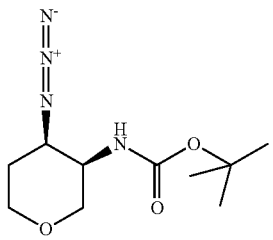 [SMILES: CC(C)(C)OC(=O)N[C@H]1COCC[C@H]1N=[N+]=[N-]]

Sodium acetate (129 g), sodium azide (102 g) and 1,5-anhydro-2,4-dideoxy-2-({[(1,1-dimethylethyl)oxy]carbonyl}amino)-3-O-(methylsulfonyl)-L-threo-pentitol (232 g) were mixed in DMF (1 l) and stirred and heated at 95° C. for 6 h. Water (2 l) was added and the mixture thoroughly mixed, ethyl acetate 1.5 l) was added and the mixture stirred for 5 min. The phases were separated, the aqueous extracted with ethyl acetate (1 l), the combined organics washed with water (2×2 l), dried and reduced to dryness in vacuo to give 1,1-dimethylethyl [(3R,4R)-4-azidotetrahydro-2H-pyran-3-yl]carbamate (153 g).

1H NMR (400 MHz, $CDCl_3$): δH 4.84(1H, bd), 3.92(2H, m), 3.76(1H, m), 3.63(2H, m), 3.52(1H, m), 1.92(2H, m), 1.46(9H, s).

1,5-anhydro-2,4-dideoxy-2-({[(1,1-dimethylethyl)oxy]carbonyl}amino)-3-O-(methylsulfonyl)-L-threo-pentitol

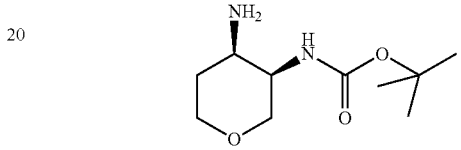

A mixture of platinum oxide and 1,1-dimethylethyl [(3R,4R)-4-azidotetrahydro-2H-pyran-3-yl]carbamate (42 g) was purged with nitrogen (×3) and ethanol (1 l) was added. The vessel was purged (×3), charged with hydrogen and stirred at 400 rpm while cooling at 20° C. and stirred for 3 h. The vessel was purged with nitrogen (×3), refilled with hydrogen and stirred for a further 3.5 h. The vessel was purged and refilled with hydrogen at 15 psi and stirred overnight. The vessel was purged and refilled and stirred for 1.5 h. The mixture was filtered through Celite under a nitrogen atmosphere, the filter cake washed with ethanol (2×500 ml) and the filtrate reduced to dryness in vacuo to give 1,1-dimethylethyl [(3R,4R)-4-aminotetrahydro-2H-pyran-3-yl]carbamate (38 g).

1H NMR (400 MHz, $CDCl_3$): δH 5.00(1H, d), 3.90(1H, m), 3.81(1H, m), 3.74 (1H, m), 3.50(1H, dd), 3.44(1H, m), 3.02(1H, m), 1.71(1H, m), 1.52-1.46(10H, m).

1,1-dimethylethyl [3R,4R)-4-({5-(aminocarbonyl)-4-[(4-methylphenyl)amino]-2-pyrimidinyl}amino)tetrahydro-2H-pyran-3-yl]carbamate

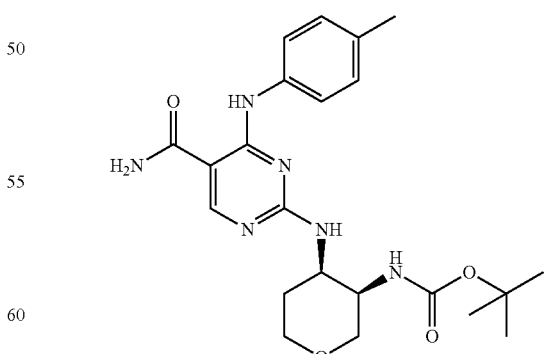

A mixture of 1,1-dimethylethyl [(3R,4R)-4-aminotetrahydro-2H-pyran-3-yl]carbamate (38 g), 2-chloro-4-[(4-methylphenyl)amino]-5-pyrimidinecarboxamide (46.2 g) and triethylamine (49.0 ml) in DMF (250 ml) was heated and stirred at 90° C. The mixture was added to water (1 l) and the solid precipitate collected by filtration. The precipitate was washed with water (2×200 ml) and dried overnight at 40° C. in vacuo.

The product was suspended in ethyl acetate (600 ml) and heated to reflux for 30 min, cooled in ice to 5° C. and the product collected by filtration. This was washed with ethyl acetate (2×100 ml) and dried at 40° C. in vacuo to give 1,1-dimethylethyl [R3R,4R)-4-({5-(aminocarbonyl)-4-[(4-methylphenyl)amino]-2-pyrimidinyl}amino)tetrahydro-2H-pyran-3-yl]carbamate (53.0 g).

LCMS (Method A): Rt 1.05 min, MH⁺ 443.

Variable temperature 1H NMR (400 MHz, D₆-DMSO, 119° C.): δH 11.21(1H, bs), 8.55(1H, s), 7.53(2H, m), 7.14 (4H, m), 6.57(1H, d), 6.01(1H, d), 4.21(1H, m), 3.91-3.78 (3H, m), 3.51-3.42(2H, m), 2.30(3H, s), 2.00-1.88(1H, m), 1.74-1.62(1H, m), 1.37(9H, s).

Example 1

2-{[(3R,4R)-3-aminotetrahydro-2H-pyran-4-yl]amino}-4-[(4-methylphenyl)amino]-5-pyrimidinecarboxamide

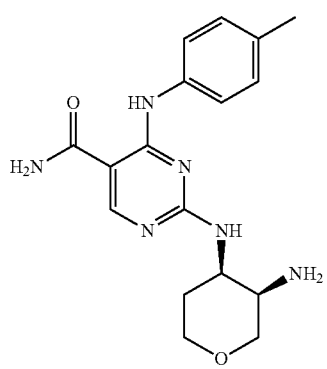 [SMILES: Cc1ccc(Nc2nc(N[C@@H]3CCOC[C@@H]3N)ncc2C(N)=O)cc1]

1,1-Dimethylethyl [(3R,4R)-4-({5-(aminocarbonyl)-4-[(4-methylphenyl)amino]-2-pyrimidinyl}amino)tetrahydro-2H-pyran-3-yl]carbamate (52.2 g) was added to a mixture of hydrogen chloride in isopropanol (5M, 300 ml) and ethanol (400 ml). The mixture was heated to reflux while stirring and heating continued for 24 h with vigorous stirring. The mixture was allowed to cool to room temperature, filtered, the solid washed with ethanol (100 ml) and dried in vacuo. The crude product was suspended in water (900 ml) and heated to reflux, giving a clear solution. The solution was basified with sodium hydroxide solution (2M, 300 ml) and cooled in ice. The precipitated product was collected by filtration, washed with water (2×100 ml) and the beige solid dried in the vacuum oven at 40° C. for 2 h to give 2-{[(3R,4R)-3-aminotetrahydro-2H-pyran-4-yl]amino}-4-[(4-methylphenyl)amino]-5-pyrimidinecarboxamide as beige solid (37.8 g).

LCMS (Method A): Rt 0.85 min, MH⁺ 343

Variable temperature 1H NMR (400 MHz, D₆-DMSO, 119° C.): δH 11.22(1H, bs), 8.55(1H, s), 7.54(2H, m), 7.14 (4H, m), 6.52(1H, bd), 4.06(1H, m), 3.83(1H, m), 3.70(1H, m), 3.53(1H, d), 3.41(1H, t), 2.96(1H, s), 2.30(3H, s), 1.89-1.65(2H, m), 1.50(2H, s).

2-{[(3R,4R)-3-aminotetrahydro-2H-pyran-4-yl]amino}-4-[(4-methylphenyl)amino]-5-pyrimidinecarboxamide (37.8 g) was heated to reflux in ethanol (1.2 liters). The hot solution was filtered through a glass scinter funnel to remove undissolved sediment and the filtrate allowed to slowly cool to room temperature, then cooled in ice to 5° C. and the solid crystalline product collected by filtration to give 2-{[(3R,4R)-3-aminotetrahydro-2H-pyran-4-yl]amino}-4-[(4-methylphenyl)amino]-5-pyrimidinecarboxamide (36.6 g) as a pale beige crystalline solid.

XRPD data were acquired on a PANalytical X'Pert Pro powder diffractometer, equipped with an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ. The time per step was 31.750 s. The sample was prepared by mounting a few milligrams of sample on a Si wafer (zero background) plate, resulting in a thin layer of powder. The spectrum thus obtained is shown as FIG. 1.

The invention claimed is:

1. A compound of formula (I):

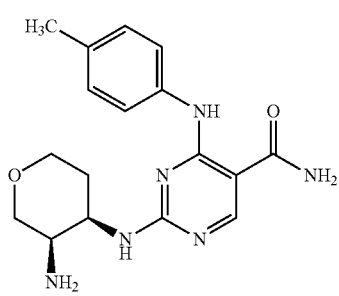

(I)

or a salt thereof.

2. A pharmaceutically acceptable salt of a compound of Formula (I) as claimed in claim 1.

3. A process for preparing a compound of formula (I) or a salt thereof according to claim 1, which process comprises the steps of:

(i) reacting a compound of formula (II):

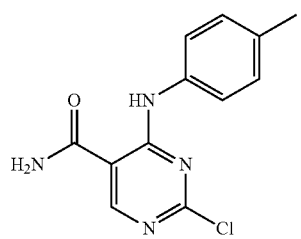

(II)

with a compound of formula (III):

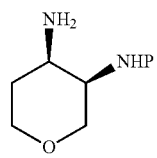

(III)

wherein P is a protecting group; and (ii) removing P.

4. A pharmaceutical composition comprising a compound of formula (I) as claimed in claim 1 or a pharmaceutically acceptable salt thereof, and one or more pharmaceutically acceptable excipients.

5. A method of treating B lymphoma tumors, which method comprises administering to a patient in need thereof an effective amount of a compound of formula (I) as described in claim 1 or a pharmaceutically acceptable salt thereof.

* * * * *